(12) United States Patent
Scagliarini et al.

(10) Patent No.: US 6,921,389 B2
(45) Date of Patent: Jul. 26, 2005

(54) SIMPLIFIED DEVICE FOR REGULATING THE FLOW RATE OF MEDICAL LIQUID DIRECTED TOWARDS A PATIENT

(75) Inventors: Massimo Scagliarini, Bologna (IT); Emanuele Bettini, Monte San Pietro (IT)

(73) Assignee: GVS S.p.A., Zola Predosa (IT)

( * ) Notice: Subject to any disclaimer, the term of this patent is extended or adjusted under 35 U.S.C. 154(b) by 101 days.

(21) Appl. No.: 10/261,599

(22) Filed: Oct. 2, 2002

(65) Prior Publication Data

US 2003/0097097 A1 May 22, 2003

(30) Foreign Application Priority Data

Nov. 20, 2001 (IT) ...................................... MI2001A2444

(51) Int. Cl.⁷ .............................. A61M 5/00; F16K 5/10
(52) U.S. Cl. ...................................... 604/248; 251/208
(58) Field of Search ................................ 604/246, 248, 604/32, 247, 30, 118, 251; 138/43; 251/208

(56) References Cited

U.S. PATENT DOCUMENTS 3,532,127 A * 10/1970 Bottone, Jr. et al. .......... 138/43
3,877,428 A * 4/1975 Seagle et al. ................ 604/248
4,011,893 A * 3/1977 Bentley ........................ 138/43
4,515,588 A * 5/1985 Amendolia .................. 604/118
5,234,413 A * 8/1993 Wonder et al. ............. 604/248

FOREIGN PATENT DOCUMENTS

FR        2 661 615        11/1991
WO        91/01155         2/1991

* cited by examiner

*Primary Examiner*—Nicholas D. Lucchesi
*Assistant Examiner*—Matthew DeSanto
(74) *Attorney, Agent, or Firm*—Young & Thompson

(57) ABSTRACT

A device for regulating the flow rate of a liquid in a medical infusion line, includes a body presenting elements for its connection to a first and to a second conduit connected to a container for the liquid and directed to a patient respectively, the body presenting a plurality of parts connected together but torsionally free about a common axis of rotation (K) to enable flow rate variation elements, associated with the body, to modify the flow rate variation elements are a plurality of recesses provided in a single part of the body, a first recess being annular and of constant depth, and at least one second recess being in the form of a broken ring and of variable depth, the recesses being concentric.

16 Claims, 5 Drawing Sheets

SIMPLIFIED DEVICE FOR REGULATING THE FLOW RATE OF MEDICAL LIQUID DIRECTED TOWARDS A PATIENT

FIELD OF THE INVENTION

The present invention relates to a device for regulating the flow rate of a liquid, such as a physiological solution, a medicament, a saline solution, etc., within a medical infusion line, in accordance with the introduction to the main claim.

BACKGROUND OF THE INVENTION

In a medical infusion line, such as a phleboclysis line, it is known to provide a device for regulating the flow rate of a liquid which is delivered by a reservoir, for example a bag, and is administered, for example intravenously, to a patient. The device is located between two conduits, namely a first conduit which departs from the reservoir and the other which leads to the patient.

Various devices of the said type are known. A known type of device comprises a body presenting three parts or portions which are connected together but are free to rotate relative to each other about a common axis of rotation. A first portion is for example connected to the first conduit (connected to the liquid reservoir), and a second portion is connected to the second conduit which leads to the patient: a third portion is disposed between the first two and has means for varying the flow rate of the liquid which is to reach the patient. These flow rate variation means comprise two recesses, namely a first recess provided in that surface of the first portion which faces the third portion and a second recess provided in that surface of the second portion which faces the third portion. A seal member is present between the various portions. The first recess is annular and is of constant depth, the second recess being in the form of a broken ring of variable depth; these are connected together by a hole provided in the third part to permanently connect the first and third recesses together. Depending on the position of this hole relative to said recesses and relative to the zones in which they are connected to the corresponding conduits, the liquid originating from the reservoir undergoes a path of greater or lesser length between the two conduit connection zones via said recesses; this results in different pressure drops in the liquid flow because of a variation in the length of the path taken within the flow regulator device with consequent modification of the liquid quantity fed to the patient, This is also aided by the variable depth of the second recess.

The known devices of the aforesaid type hence comprise a body with five elements (the three portions and the two seal members between them) which is costly to produce and assemble, is costly to stock and is of large dimensions. A device of the aforesaid type is also known having a structure in which the flow rate variation means comprise a body of the aforedescribed type, but in which the recesses are connected together by a channel provided in a cylindrical side wall. This device does not offer adequate and precise regulation of the flow rate of the liquid directed to the patient, and moreover its regulation is more difficult that that of the other aforedescribed known type of device.

SUMMARY OF THE INVENTION

An object of the present invention is to provide a device for regulating the flow rate of the medicinal liquid directed towards a patient which is of more simple construction than analogous known devices, is of reliable and simple use and enables more precise regulation of the flow rate than that obtainable with known devices.

Another object is to provide a device with a small number of parts which is more economical than analogous known devices and which simplifies and limits its production and assembly operations and its storage costs.

These and further objects which will be apparent to the expert of the art are attained by a device in accordance with the accompanying claims.

BRIEF DESCRIPTION OF THE DRAWINGS

The present invention will be better understood from the accompanying drawing, which is provided by way of non-limiting example and in which.

DETAILED DESCRIPTION OF THE INVENTION

With reference to said figures, a device according to the invention is indicated overall by 1. It comprises a body 2 presenting a first part or portion 3 to be connected to a first conduit (not shown) of a medical infusion line connected to a container or reservoir of medicinal liquid, and a second part or portion 4 to be connected to a second conduit of said line (also not shown) carrying the said liquid to a patient.

Figure 5:
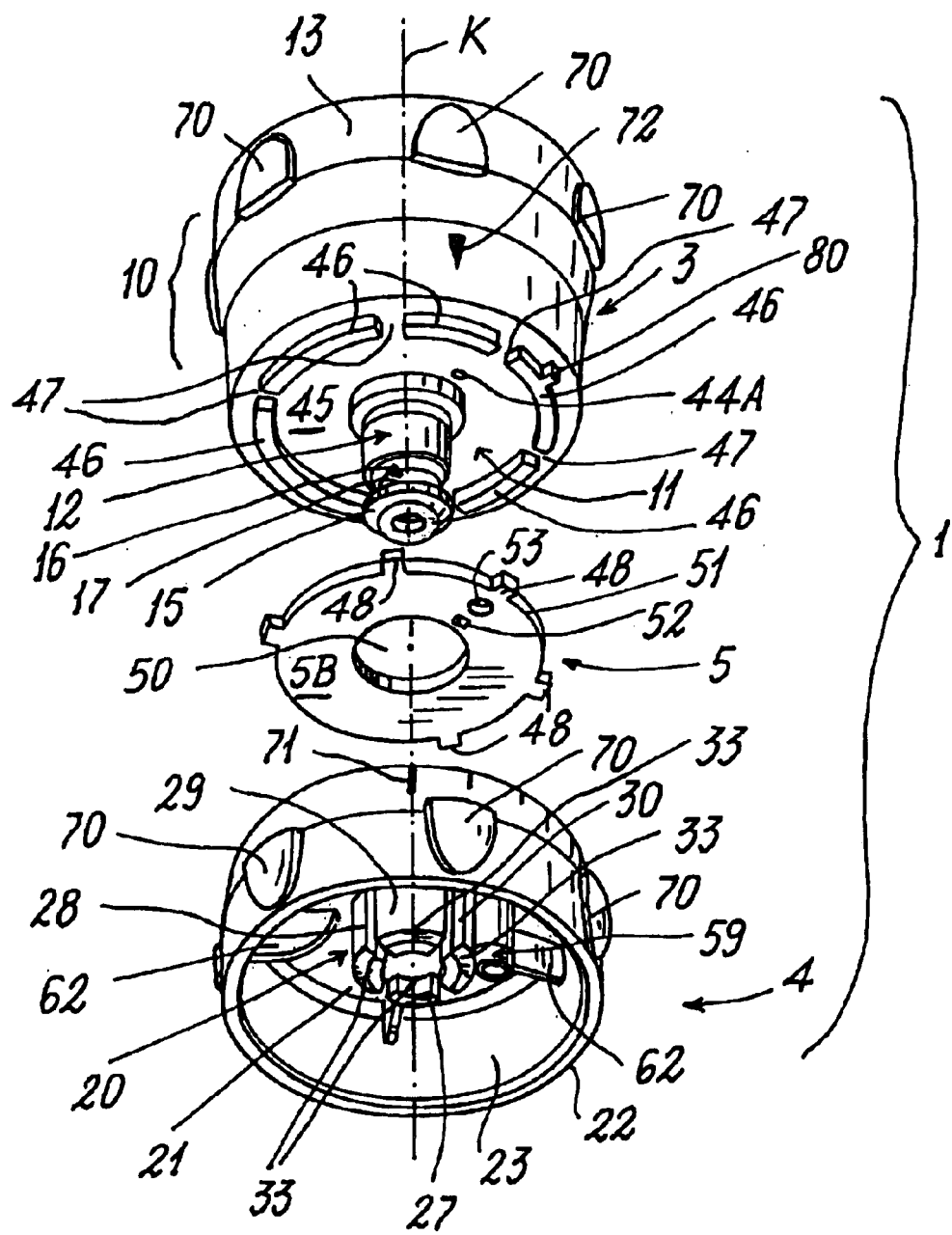
FIG. 5 is an exploded sectional view of the device of FIG. 1 seen from below.
Figure 6:
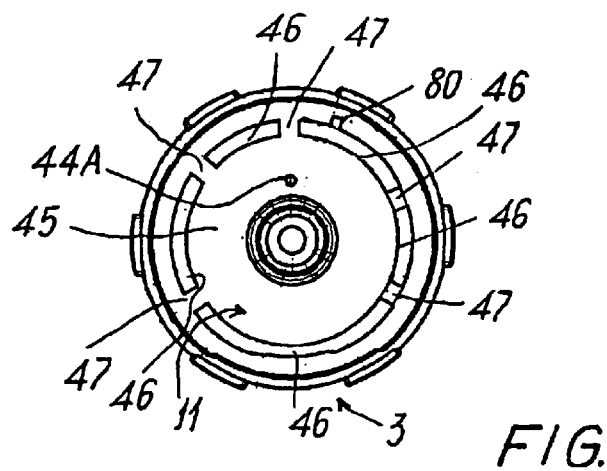
FIG. 6 is a view from below of a first part of the device of FIG. 1.
Figure 7:
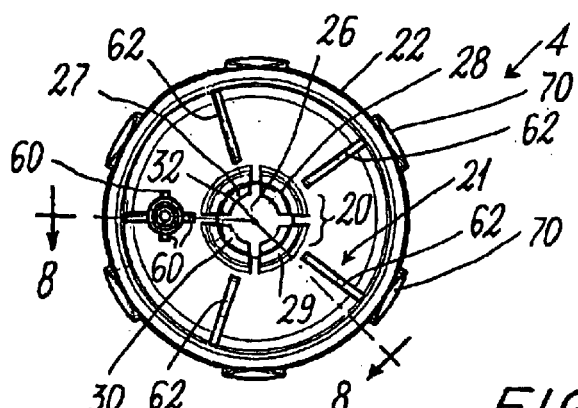
FIG. 7 is a view from below of a second part of the device of FIG. 1.

Between the first part 3 and the second part 4 there is a seal element or gasket 5. These parts are connected together but are torsionally independent of each other such that they can rotate about a common axis K or longitudinal axis of the body 2 (see for example FIG. 5). To achieve said connection, the first part 3 comprises a structure 10 of substantially cup shape and having a flat portion 11 from which there projects towards the part 4 a connection element 12 hollow at 12A, and from the edge of which there rises a wall 13 defining a cavity 14. The connection element 12 presents a head 15 in which a recess 16 is present defining an undercut 17 in correspondence with said head. The cavity 12A of said element 12 opens into the portion 11.

The connection element 12 is arranged to be inserted into a connection counter-element 20 of the second part 4. The counter-element 4 projects from a flat portion 21 of the part 4, from the edge of which there rises a wall 22 the surface of which defines a cavity or compartment containing the counter-element 20.

Figure 8:
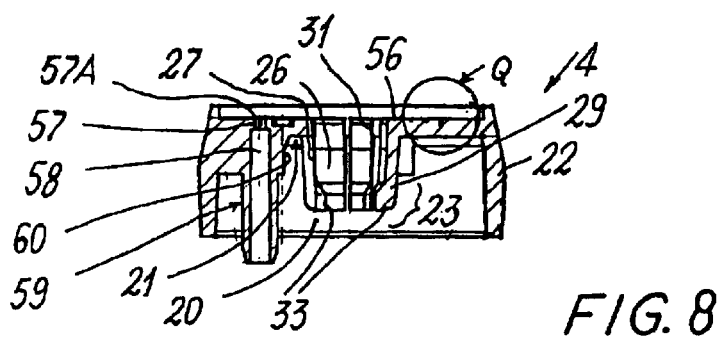
FIG. 8 is a section on the line 8—8 of FIG. 7.
Figure 9:
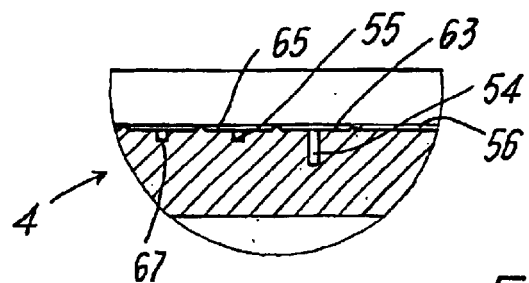
FIG. 9 is an enlarged view of that part of FIG. 8 indicated by Q.

This latter is internally hollow at 26. In this respect, the cavity 26 is bounded by a plurality of walls 27, 28, 29 and 30 having a first cylindrical portion 31 (see FIG. 8) acting as a centering element when connecting the connection element 12 to the counter-element 20. The walls 27, 28, 29 and 30 are in the form of a circular arc in section, and are disposed along a circumference about a common centre 32 lying on the axis K. These walls, separated from each other, are elastically movable relative to each other to enable the element 12, when being coupled to the counter-element 20, to pass into the cavity 26. Each wall 27, 28, 29 and 30 presents an end 33 bent into the cavity 26 to cooperate with the recess 16 in the element 12 and with its head 15, to retain it (removably) coupled to the counter-element 20. By flexing the walls 27, 28, 29 and 30 outwards the element 12 can be separated from the counter-element 20 (and hence the part 3 from the part 4), even though with difficulty.

The part 3 presents, projecting from a face 11A of the flat portion 11 and into the cavity 14, a plurality of stiffening ribs 38 and a connection element 40 to be connected to the first conduit of the medical line. Fins 41 on the base 42 of the connection element 40 act as a limit stop for the insertion of this latter into the said first conduit. The connection element 40 is hollow at 43; this cavity is connected to a through hole 44 in the flat portion 11 which opens at 44A into a free face 45 of that portion (opposite the face 11A) from which the connection element 12 projects. On the face 45 there are also present a plurality of arc-shaped projections 46 positioned along a circumference with its centre on the longitudinal axis K of the body 2 (and of the part 3). These projections 46 are spaced apart by apertures 47 within which lugs 48 of the gasket 5 are housed so that this latter is torsionally coupled to the part 3 of the body 2. These projections 46 have at least partly different shapes (or a lesser or greater length) so that the lugs 48 can be inserted into the apertures 47 only in one precise manner. The distance between the lugs 48 is also different from one lug to another to correspond to the distances between adjacent apertures 47.

The gasket 5 is flat and annular and presents a central through hole 50 to receive the element 12. The lugs project radially from the outer edge 51 of the gasket.

The gasket 5 has a first surface 5A facing the first part or portion 3 of the body 2 of the device 1, and a second surface 5B (opposite the first) facing the second part or portion 4 of said body 2. The gasket comprises a through hole 52 to be disposed coaxially with the hole 44 of the part 3, and presents in the surface 5B a dead hole 53. This latter connects together two recesses 54 and 55 present in a flat free face 56 of the flat portion 21 of the part 4 of the body 2 on which the gasket 5 lies. The first recess 54 is annular and communicates with an aperture 57A of a hole 57 provided in the portion 21 and communicating with a cavity 58 of an element 59 connecting the part 4 to the second conduit of the said medical infusion line. This element projects from the portion 21 into the cavity 23 of the part 4 and at its base there are fins 60 present to act as a limit stop for the connection to the said second conduit. Stiffening ribs 62 also project from the portion 21 and into the cavity 23.

With regard to the recesses 54 and 55, the first recess 54, as stated, is of annular shape and presents a constant depth. It opens into a laterally flared groove 63 in the face 56 of the portion 21. In contrast, the second recess 55 is of open-ring shape and of a depth which varies from one end 55A to the other end 55B. It opens into a flared-edge groove 65 in the face 56.

At the end 55A a dead hole 66 is present connecting the recess 55 to a third recess 67, shaped as the second 55. In this embodiment of the part 4, the through hole 50 of the gasket 5 opens in correspondence with the recess 67, this being the most inner in the face 56 of the portion 21. In the absence of the recess 67 or if the recesses were of even number, the element 40 would be connected directly to the said recess 55. In this case the shape of the parts 3 and 4 would be different from that shown in the figures and the part 4 would present both the connection element 59 and the connection element 40. The gasket 5 would also not be provided with the through hole 52 and would present only the dead hole 53 to connect the recesses 54 and 55 together.

On the outside of the walls 13 and 22 of the parts 3 and 4 projections 70 are present acting as anti-slip gripping elements to facilitate relative rotation between the parts 3 and 4 in order to modify in a predefined required manner the flow rate of the liquid transiting through the body 2 of the device 1. The definition of the flow rate is indicated by a plurality of notches 71 and by a reference mark 72 provided on the part 4 and on the part 3 (or vice versa) respectively. The different length of the notches indicates the different flow rates obtainable by means of the body 2 of the device 1.

Figure 1:
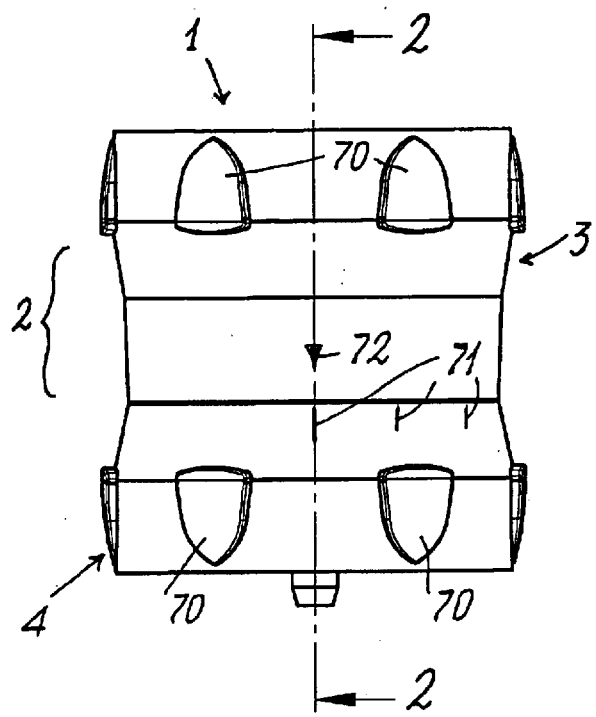
FIG. 1 is a front view of a device according to the invention.
Figure 2:
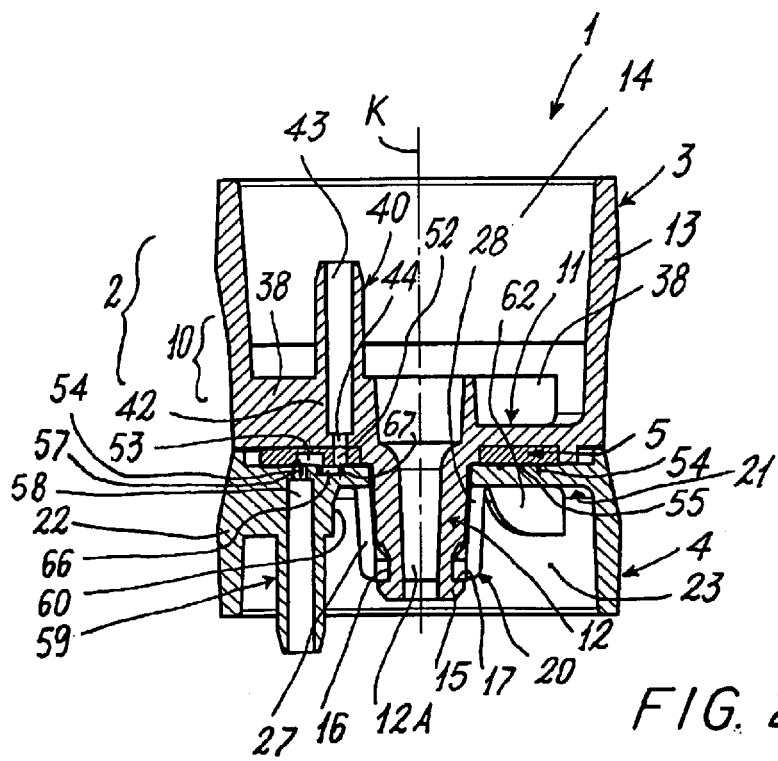
FIG. 2 is a section on the line 2—2 of FIG. 1.
Figure 3:
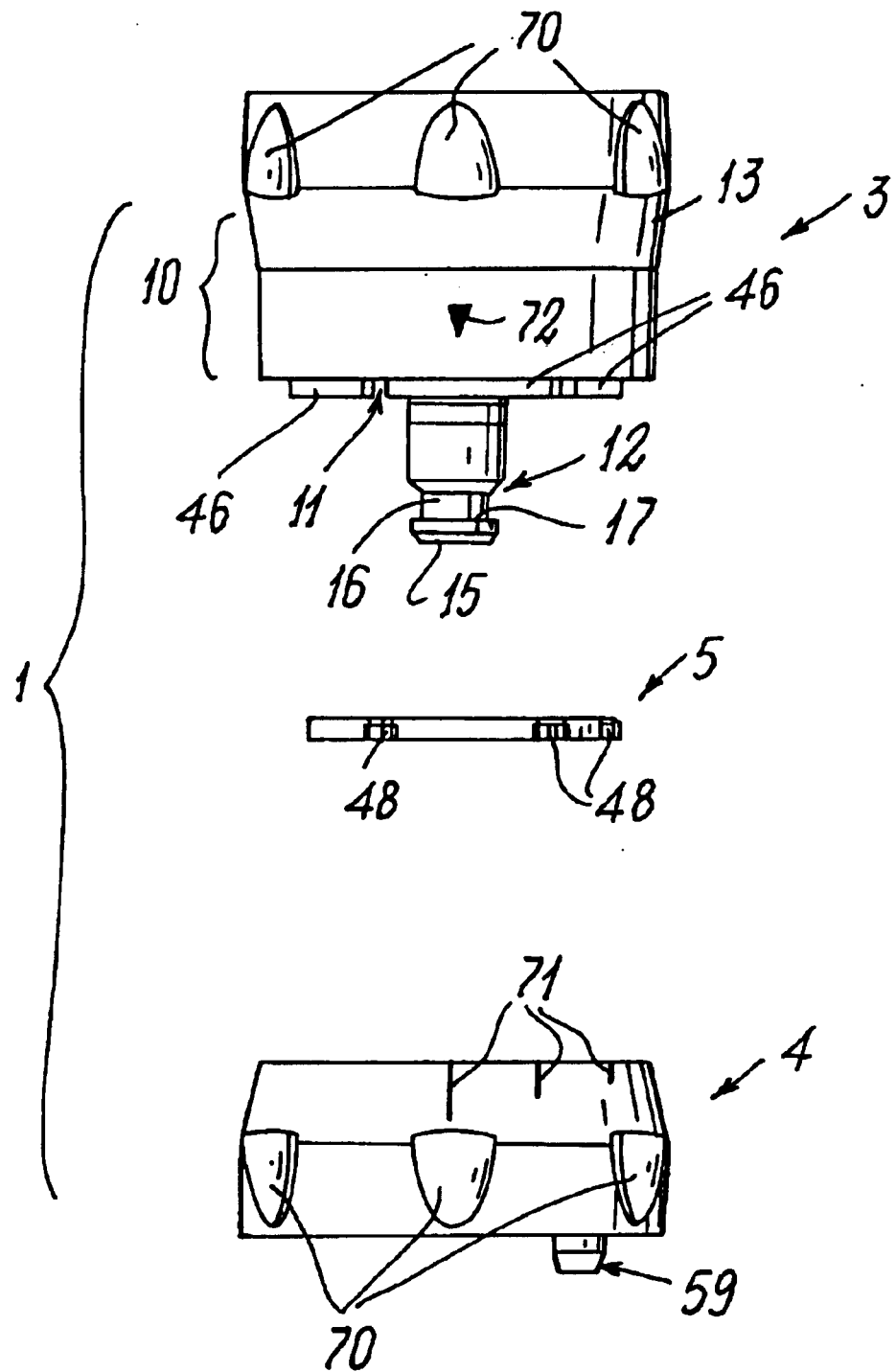
FIG. 3 is an exploded front view of the device of FIG. 1.
Figure 4:
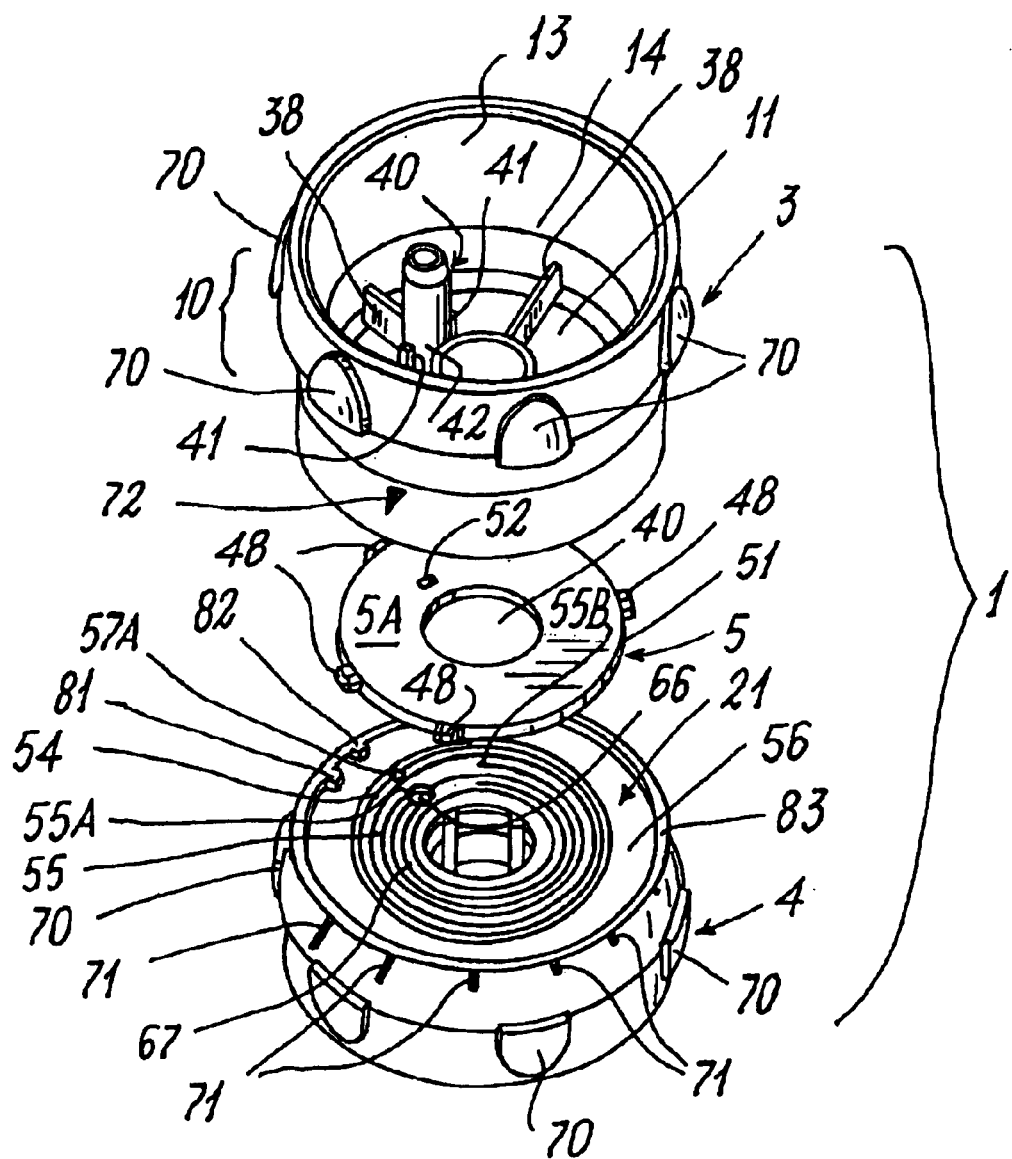
FIG. 4 is an exploded sectional view of the device of FIG. 1 seen from above.

The flow rate variation is achieved by moving the part 3 relative to the part 4 about the axis K. It will be assumed that the device is in the condition shown in FIG. 2 in which the hole 44, the hole 52 and the hole 66 are coaxial. In this case, the dead hole 53 directly connects the hole 66 to the annular recess 54 of constant section and depth and in particular to the aperture 57A of the hole 57 which opens into said recess 54. Hence the liquid passing from the first conduit of the medical line into the cavity 43 of the connection element 40 of the first part 3 passes, without varying its flow rate, into the cavity 58 of the connection element 59 of the second part 4 and from there into the second conduit of the medical line.

If this flow rate is to be varied, the part 3 is rotated relative to the part 4 about the axis K. In this case, the hole 52 in the gasket 5 moves away from the dead hole 66 to assume any position between the ends of the recess 67. The liquid arriving from the hole 52 hence passes into the open-ring recess 55 via the dead hole 66. This liquid passes into the recess 55 to fill it as far as the position of said recess faced by the dead hole 53 of the gasket 5. The liquid passes through this hole and into the recess of constant section 54 and from there, on reaching the hole 57, it can pass through the connection element 59 and into the second conduit of the medical line. The more the part 3 is rotated to increase the distance of the through hole 52 of the gasket 5 from the dead hole 66, the greater the reduction in the flow rate of the liquid directed towards the second conduit of the medical line. To achieve reliable regulation of this flow rate, a limit stop is provided for the relative rotation between the parts 3 and 4 in correspondence with the coaxial portion between the hole 52 and the dead hole 66. This limit stop is defined by a tooth 80 jutting from a projection 46 on the part 3 to cooperate with teeth 81 and 82 jutting from a edge 83 rising from the face 56 of the flat portion 21 of the part 4. When the tooth 81 cooperates with the tooth 80 the position of substantially zero reduction of the flow rate is defined, the position of maximum reduction (achieved by the pressure drop in the liquid stream obtained by prolonging the path travelled within the body 2 of the device 1) being achieved when the tooth 80 rests against the tooth 82.

By virtue of the coplanar position of the (concentric) recesses 54, 55 and 67 (all provided within the flat face 56 of the portion 21 of the part 4) it is possible to very precisely regulate the quantity of medical liquid fed to the patient. To obtain said recesses (or at least two of them, namely the recess of constant annular section 54 and one of variable section 55 or 67) is a simple matter, the flow rate regulation also being simple and reliable. Moreover, the body 2, having a smaller number of components than analogous elements of known devices for regulating flow rate in a medical line, is of lower production and storage cost than known devices.

A preferred embodiment of the invention has been described. However in the light of the aforegoing description and within the scope of the ensuing claims other devices similar to that of the figures can be obtained. For example, the gasket 5 can in effect be a portion of the part 3, integral with it, obtained for example by known co-moulding or over-moulding methods; alternatively the number of broken ring recesses can be from two to any number n, to enable the flow rate of medical liquid passing through the device to be even more finely varied. In that case the gasket 5 presents a plurality of dead holes 53, whereas the part 4 presenting the recesses comprises a plurality of dead holes 66. These latter alternate with the holes 53 to connect the recesses of the part 4 together in pairs. These variants are also to be considered as falling within the scope of the present document.

What is claimed is:

1. A device for regulating the flow rate of a liquid in a medical infusion line, which comprises:
    a body having connection elements for connection to a first and to a second conduit;
    the first conduit being connected to a container of said liquid and the second conduit being directed to a patient to whom the liquid is to be administered;
    the body comprising a first part, a second part, and a seal element interposed therebetween;
    said parts being connected together but torsionally independent of each other such that said parts are rotatable about a common axis of rotation enabling flow rate variation means, associated with the body, to modify the flow rate of the liquid fed to the patient;
    the flow rate variation means comprising a plurality of concentric recesses provided in the second part of said body;
    communication means being provided above said plurality of recesses and associated with the first part of said body to connect at least a first recess to a second recess;
    one recess chosen from said first recess and second recess being connected to the first conduit and the other of said first and second recess being connected to the second conduit;
    said first recess being annular and of constant depth and said second recess being in the form of a broken ring and of variable depth;
    the flow rate variation means being provided in the second part of the body connected to the second conduit;
    said communication means comprising a through hole provided within the seal element and a dead hole provided within that surface of said seal element which faces the flow rate variation means; said dead hole not going through to an opposite surface of said seal element; and
    said dead hole structured and arranged to connect in series the first and the second recesses in the second part of the body.

2. The device according to claim 1, wherein the seal element is torsionally rigid with the first part of the body.

3. The device according to claim 2, wherein the first part comprises a flat portion having an edge, from which rises a wall defining a cavity having a hollow connection element to connect the first part to the first conduit; said connection element projecting from a face of the flat portion; the cavity cooperating with a through hole provided in the flat portion and opening into a free face of said flat portion; said free face comprising a plurality of restraining means for the seal element.

4. The device according to claim 3, wherein the restraining means for the seal element comprise a plurality of projections spaced apart along a circumference having its center on the axis of rotation, at least part of said projections having dimensions which differ from each other in order to define the only way of fitting the seal element.

5. The device according to claim 4, further comprising stop means provided on the first and second parts of the body, for limiting the relative rotary movement between the first and second parts about the axis of rotation.

6. The device according to claim 5, wherein the stop means comprise at least one element jutting from one of the projections of the first part, said at least one element being arranged to cooperate with at least one counter-element provided in correspondence with an edge of the flat portion of the second part.

7. The device according to claim 4, wherein the seal element has an annular flat shape and a plurality of lugs jutting from its outer edge, said lugs being spaced apart at a non-uniform distance and being able to cooperate in only one way with apertures positioned at irregular distances apart between the projections present on the free face.

8. The device according to claim 1, wherein the seal element is a portion of the first part of the body.

9. The device according to claim 8, further comprising releasable coupling means associated with the two parts of the body to enable said two parts to be axially coupled together.

10. The device according to claim 9, wherein the coupling means comprise, associated with the first part, an element projecting from the flat portion of said first part and presenting a head in which a groove is laterally provided, and, associated with the second part, a coupling element which receives in its cavity the element projecting from the first part, and is able to deform and to clamp elastically against said element of the first part to hence retain it.

11. The device according to claim 10, wherein the coupling element comprises a plurality of spaced-apart arcuate walls which are disposed along a circumference with its center on the rotational axis of the device, to define the cavity into which the element projecting from the first part is insertable, and each arcuate wall having an end bent into said cavity in order to cooperate with the groove of said element.

12. The device according to claim 8, further comprising a plurality of concentric broken-ring recesses of variable depth, one of said recesses communicating with the through hole of the seal element, said recesses being connected together by a dead hole provided in that face of the flat portion in which the recesses are provided, the second recess communicating with the first recess via the dead hole provided in the seal element overlying said flat portion.

13. The device according to claim 8, further comprising stop means provided on the first and second parts of the body, for limiting the relative rotary movement between the first and second parts about the axis of rotation.

14. The device according to claim 8, wherein the first and the second parts of the body comprise means for indicating the flow rate of the liquid transiting through said body.

15. The device according to claim 1, wherein the flow rate variation means are provided in a free flat face of a flat portion of the second part connected to the second conduit.

16. The device according to claim 1, wherein the first recess of constant depth communicates with a through hole provided in the flat portion of the second part; said through hole communicating with a cavity provided in a connection element to said second conduit and hence with said second conduit.

* * * * *